(12) United States Patent
Chiang

(10) Patent No.: US 10,632,162 B2
(45) Date of Patent: Apr. 28, 2020

(54) **HYDROLYSATE OF WATER EXTRACT OF *GRACILARIOPSIS CHIANGII*, AND PREPARATION PROCESS AND USE THEREOF**

(71) Applicant: MHBT CO., LTD., Douliou, Yunlin County (TW)

(72) Inventor: Chun-Hui Chiang, Douliou (TW)

(73) Assignee: MHBT CO., LTD., Douliou (TW)

( * ) Notice: Subject to any disclaimer, the term of this patent is extended or adjusted under 35 U.S.C. 154(b) by 363 days.

(21) Appl. No.: 15/409,131

(22) Filed: Jan. 18, 2017

(65) Prior Publication Data

US 2018/0104290 A1  Apr. 19, 2018

(30) Foreign Application Priority Data

Oct. 14, 2016 (TW) .............................. 105133262 A

(51) Int. Cl.
*A61K 36/04* (2006.01)
*A61Q 19/00* (2006.01)
*A61K 8/9717* (2017.01)
*A61Q 19/08* (2006.01)

(52) U.S. Cl.
CPC ............ *A61K 36/04* (2013.01); *A61K 8/9717* (2017.08); *A61Q 19/00* (2013.01); *A61K 2236/15* (2013.01); *A61K 2236/331* (2013.01); *A61K 2236/50* (2013.01); *A61K 2236/53* (2013.01); *A61Q 19/08* (2013.01)

(58) Field of Classification Search
CPC ...................................................... A61K 36/04
See application file for complete search history.

(56) References Cited

PUBLICATIONS

Shiu-Feng Huang et. al., (Jul. 2011) Functional properties of hydrolyzed proteins from red seaweed *Gracilaria tenuistipitata*, Journal of National Kaohsiung Marine University, Kaohsiung, Taiwan.
Yong-Yue Kang et. al., (Aug. 2010), The effects of Gracilaria tenuistipita extracts on antioxidant capacity and on the functional properties in skin-care products , Journal of National Kaohsiung Marine University, Kaohsiung, Taiwan.
Jing-Iong Yang et al. (2012), Antiradical properties of protein extracts from red seaweed *Gracilaria tenuistipitata*, Journal of National Kaohsiung Marine University, 26:43-54, Kaohsiung, Taiwan.
Search Report appended to an Office Action issued in Taiwanese counterpart Application No. 105133262, dated Mar. 20, 2017 (1 page), and corresponding English translation.

*Primary Examiner* — Amy L Clark
(74) *Attorney, Agent, or Firm* — Hamre, Schumann, Mueller & Larson, P.C.

(57) ABSTRACT

Disclosed herein are a hydrolysate of water extract of *Gracilariopsis chiangii* and a preparation process thereof. Also disclosed herein is a composition including the aforesaid hydrolysate of water extract of *Gracilariopsis chiangii*. The composition can be used in enhancing the moisture-retaining capacity of the skin, improving wound healing and reducing oxidative stress.

15 Claims, 5 Drawing Sheets

HYDROLYSATE OF WATER EXTRACT OF *GRACILARIOPSIS CHIANGII*, AND PREPARATION PROCESS AND USE THEREOF

CROSS-REFERENCE TO RELATED APPLICATION

This application claims priority of Taiwanese Patent Application No. 105133262, filed on Oct. 14, 2016.

FIELD

The disclosure relates to a hydrolysate of water extract of *Gracilariopsis chiangii* and a preparation process thereof. This disclosure also relates to a composition including the hydrolysate of water extract of *Gracilariopsis chiangii*, which is suitable for enhancing the moisture-retaining capacity of the skin, improving wound healing and reducing oxidative stress.

BACKGROUND

The skin is the first line of defense against external factors, and plays a key role in protecting the body against water loss, pathogens and various harmful environments. Ultraviolet (UV), ionizing radiation, and certain medications or xenobiotics might induce production of ROS and free radicals. Oxidative stress occurs when ROS and free radicals exceed the antioxidant capacity of cells or tissues. Thereafter, ROS and free radicals react with components within the cell (e.g., DNA, proteins, lipids, etc.), thereby resulting in undesired oxidative damage to the skin. It has been reported that ROS and free radicals cause delay of wound healing.

When a wound results from skin damage (such as scald, trauma, surgical injury or contusion), an inflammatory response is triggered at the wound site where a large amount of ROS and free radicals are released to assist immune cells in fighting against the pathogenic bacteria. However, excessive ROS and free radicals might harm the tissues surrounding the wound. During the wound healing process, fibroblasts migrate to the wound site and then proliferate there, thereby resulting in angiogenesis, epithelialization and collagen remodeling. Excessive ROS and free radicals not only inhibit angiogenesis, but also inactivate the enzymes involved in the signaling pathways related wound healing, thereby interrupting wound healing.

*Gracilaria* sp. and *Gracilariopsis* sp., are common red algae belonging to Phylum Rhodophyta, Class Florideophyceae, Order Gracilariales and Family Gracilariaceae. These red algae need sufficient illumination to grow up, and mainly reside in the surface layer of seawater (0~25° C.) in temperate and tropical regions. Since *Gracilaria* sp. and *Gracilariopsis* sp. are high in dietary fiber, high in proteins, low in fats, and rich in vitamins, minerals, unsaturated fatty acids, polysaccharides and carotenoids, these two algal species have important economic values. It has been known that *Gracilaria* sp. and *Gracilariopsis* sp. may be biologically effective in antioxidation, enhancing immune responses, lowering fats and anti-cancer actions.

It has been reported that the protein extracts from red algae *Gracilaria tenuistipitata* (GT), which are produced by treating GT with proteinase bromelain and then conducting ammonium sulfate precipitation, have antiradical properties (Jing-Iong Yang et al. (2012), *Journal of National Kaohsiung Marine University*, 26:43-54).

In spite of the aforesaid, researchers in this field endeavor to look for extracts from other red algae species having useful biological activity.

SUMMARY

Therefore, in a first aspect, this disclosure provides a process for preparing a hydrolysate of water extract of *Gracilariopsis chiangii*, including:
subjecting a *Gracilariopsis chiangii* alga to an extraction treatment with water so as to obtain a water extract; and
subjecting the water extract to a hydrolysis treatment with bromelain.

In a second aspect, this disclosure provides a hydrolysate of water extract of *Gracilariopsis chiangii*, which is prepared by a process including:
subjecting a *Gracilariopsis chiangii* alga to an extraction treatment with water so as to obtain a water extract; and
subjecting the water extract to a hydrolysis treatment with bromelain.

In a third aspect, this disclosure provides a composition including the aforementioned hydrolysate of water extract of *Gracilariopsis chiangii*.

The hydrolysate of water extract of *Gracilariopsis chiangii* has been demonstrated to be effective in enhancing the moisture-retaining capacity of the skin, improving wound healing and reducing oxidative stress. Therefore, in the forth aspect, this disclosure provides a method for enhancing the moisture-retaining capacity of the skin, including administering to a subject the aforementioned composition.

In a fifth aspect, this disclosure provides a method for improving wound healing, including administering to a subject the aforementioned composition.

In a sixth aspect, this disclosure provides a method for reducing oxidative stress, including administering to a subject the aforementioned composition.

BRIEF DESCRIPTION OF THE DRAWING

Other features and advantages of the disclosure will become apparent in the following detailed description of the embodiments with reference to the accompanying drawing, of which.

DETAILED DESCRIPTION

Figure 1:
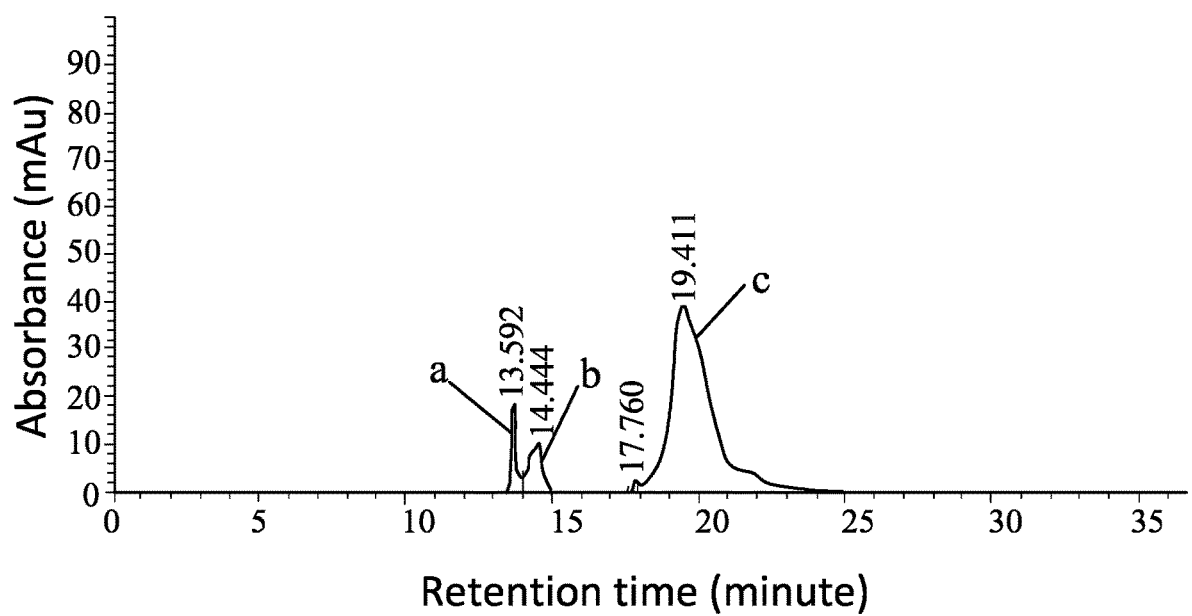
FIG. 1 is a HPLC elution profile regarding a hydrolysate of water extract of *Gracilariopsis chiangii* (designated as HWEGC) prepared in Example 1.

Unless defined otherwise, all technical and scientific terms used herein have the meaning commonly understood by a person skilled in the art to which the present disclosure belongs.

One skilled in the art will recognize many methods and materials similar or equivalent to those described herein, which could be used in the practice of the present disclosure. Indeed, the present disclosure is in no way limited to the methods and materials described.

In order to develop a skin protection composition that is safe for long term use, the applicants have attempted to obtain extracts of *Gracilariopsis chiangii* using various methods. The applicants have further found that a hydrolysate, which is prepared by subjecting a water extract of *Gracilariopsis chiangii* to a hydrolysis treatment with bromelain, is more effective in performing antioxidation action, improving wound-healing and enhancing the moisture-retaining capacity of the skin as compared to the water extract from which it is prepared.

Accordingly, this disclosure provides a hydrolysate of water extract of *Gracilariopsis chiangii* and a process for preparing the same. The hydrolysate of water extract of *Gracilariopsis chiangii* according to this disclosure may be prepared by a process including:

subjecting a *Gracilariopsis chiangii* alga to an extraction treatment with water so as to obtain a water extract; and subjecting the water extract to a hydrolysis treatment with bromelain.

In certain embodiments, the *Gracilariopsis chiangii* alga to be extracted may be a fresh alga of *Gracilariopsis chiangii*. In certain embodiments, prior to the extraction treatment, the *Gracilariopsis chiangii* alga may be subjected to a pre-treatment selected from drying treatment, grinding treatment, shredding treatment, pulverizing treatment or combinations thereof.

According to this disclosure, the weight ratio of the *Gracilariopsis chiangii* alga to water ranges from 1:0.5 to 1:5. In an embodiment of this disclosure, the weight ratio of the *Gracilariopsis chiangii* alga to water is 1:1.25.

According to this disclosure, the extraction treatment with water may be conducted at a temperature ranging from 35° C. to 65° C. In an embodiment of this disclosure, the extraction treatment with water may be conducted at 50° C.

It should be noted that the conditions for the extraction treatment with water may vary depending on the factors (such as the pre-treatment of the *Gracilariopsis chiangii* alga, the weight ratio of the *Gracilariopsis chiangii* alga to water, etc.) so as to achieve the desired extraction result.

According to this disclosure, the weight ratio of bromelain to the water extract ranges from 1:50 to 1:500. In an embodiment of this disclosure, the weight ratio of bromelain to the water extract is 1:180.

According to this disclosure, the hydrolysis treatment with bromelain may be conducted at a temperature ranging from 30° C. to 60° C. for 3 hours to 6 hours. In an embodiment of this disclosure, the hydrolysis treatment with bromelain may be conducted at 45° C. for 4 hours.

It should be noted that the conditions for the hydrolysis treatment with bromelain may vary depending on the factors (such as the weight ratio of the water extract to bromelain, etc.,) so as to achieve the desired hydorlysis result.

In certain embodiments, the process may further include conducting a solid-liquid separation treatment after the hydrolysis treatment so as to remove a solid portion resulting from the hydrolysis treatment. The solid-liquid separation treatment may be conducted using technology well known to those skilled in the art. Examples of the solid-liquid separation treatment include, but are not limited to, filtration, centrifugation and decantation. In an embodiment of the disclosure, the solid-liquid separation treatment includes a centrifugation step and a subsequent filtration step.

The results of the preliminary human tests done by the applicants show that the hydrolysate of water extract of *Gracilariopsis chiangii* can increase the water content of stratum corneum without incurring undesired side effects. Therefore, the hydrolysate of water extract of *Gracilariopsis chiangii* according to this disclosure is expected to be useful in enhancing the moisture-retaining capacity of the human skin.

Accordingly, this disclosure provides a composition including the aforesaid hydrolysate of water extract of *Gracilariopsis chiangii*. Such composition can be used for enhancing the moisture-retaining capacity of the skin.

This disclosure further provides a method for enhancing the moisture-retaining capacity of the skin. The method includes administering to a subject the composition described above. An effective amount of the composition may be administered for a sufficient time until the moisture-retaining capacity of the skin to be applied is significantly enhanced. The effective amount of the composition would not cause an adverse side effect to the skin.

In certain embodiments, the composition is a pharmaceutical composition.

The pharmaceutical composition according to this disclosure can be formulated into a suitable dosage form for oral or topical administration using technology well known to those skilled in the art.

The pharmaceutical composition according to this disclosure can additionally include a pharmaceutically acceptable carrier widely employed in the art of drug-manufacturing. For instance, the pharmaceutically acceptable carrier may include one or more of the following agents: solvents, buffers, emulsifiers, suspending agents, decomposers, disintegrating agents, dispersing agents, binding agents, excipients, stabilizing agents, chelating agents, preservatives, wetting agents, lubricants, diluents, absorption delaying agents, liposomes, sweetening agents, flavoring agents, coloring agents, etc. The choice and amount of the pharmaceutically acceptable carrier are within the expertise of those skilled in the art.

Examples of the oral dosage form include, but are not limited to, aseptic power, tablets, troches, lozenges, pellets, capsules, dispersible powder or granule, solutions, suspensions, emulsions, syrup, elixir, slurry, etc.

Examples of the topical dosage form include, but are not limited to, emulsions, gels, ointments, cream, patches, liniments, powder, aerosol, spray, lotions, serum, paste, foam, drops, suspensions, salve, bandages, etc.

In an exemplary embodiment of this disclosure, the pharmaceutical composition is formulated into an external preparation by admixing the hydrolysate of water extract of *Gracilariopsis chiangii* with a base that is well known and commonly used in the art.

According to this disclosure, suitable bases may include one or more of the following additives: water, alcohol, glycol, hydrocarbons (such as petroleum jelly and white petrolatum), wax (such as paraffin and yellow wax), preserving agents, antioxidants, surfactants, absorption enhancers, stabilizing agents, gelling agents (such as carbopol 974P, microcrystalline cellulose and carboxymethylcellulose), active agents, humectants, odor absorbers, fragrance, pH adjusting agents, chelating agents, emulsifiers, occlusive agents, emollients, thickeners, solubilizing agents, penetration enhancers, anti-irritants, colorants, propellants, etc. The choice and amount of these additives are within the expertise of those skilled in the art.

According to the disclosure, the dosage and frequency of administration of the pharmaceutical composition for enhancing the moisture-retaining capacity of the skin may vary depending on the following factors: the initial condition of the skin area to be subjected to the enhancement of the moisture-retaining capacity, the route of administration, and the desired moisture-retaining effect to be achieved. For instance, the dosage of the pharmaceutical composition for topical administration according to this disclosure may be 1-10 mg/cm$^2$ of the skin area, and may be administered one to three times per day. In certain embodiments, the dosage of the pharmaceutical composition for oral administration may be 0.05-5 mg/Kg, and may be administered one to three times per day.

In addition, the hydrolysate of water extract of *Gracilariopsis chiangii* according to this disclosure has been proven to be effective in improving the fibroblast-mediated wound closure. As such, it is contemplated that the hydrolysate of water extract of *Gracilariopsis chiangii* according to this disclosure can be used in the improvement of wound healing.

Therefore, the composition provided in this disclosure can be used for improving wound healing. The present disclosure further provides a method for improving wound healing, which includes administering to a subject the composition described above. An effective amount of the composition may be administered for a sufficient time until the wound area is significantly decreased. The effective amount of the composition would not cause an adverse side effect to the wound.

In certain embodiments, the composition for improving wound healing is a pharmaceutical composition. The administration route, dosage and pharmaceutically acceptable carrier of this pharmaceutical composition are similar to those described above for the pharmaceutical composition for enhancing the moisture-retaining capacity of the skin.

According to the disclosure, the dosage and frequency of administration of the pharmaceutical composition for improving wound healing may vary depending on the following factors: the severity of the wound to be treated, the route of administration, and the desired healing effect to be achieved. For instance, the dosage of the pharmaceutical composition for topical administration according to this disclosure may be 1-10 mg/cm$^2$ of the skin area, and may be administered one to three times per day. In certain embodiments, the dosage of this pharmaceutical composition for oral administration may be 0.05-5 mg/Kg, and may be administered one to three times per day.

Furthermore, the hydrolysate of water extract of *Gracilariopsis chiangii* according to this disclosure has been proven to have excellent DPPH free radical-scavenging activity and reducing activity. As such, it is contemplated that the hydrolysate of water extract of *Gracilariopsis chiangii* according to this disclosure can be used as an antioxidant and a free radical scavenger for reducing oxidative stress.

Therefore, the composition provided in this disclosure can be used for reducing oxidative stress. The present disclosure further provides a method for reducing oxidative stress, which includes administering to a subject the composition described above. The composition may be administered to the subject in an effective amount for a sufficient time until the oxidative stress is significantly reduced. The effective amount of the composition would not cause adverse side effects to the subject.

In certain embodiments, the composition for reducing oxidative stress is a pharmaceutical composition. The administration route, dosage and pharmaceutically acceptable carrier of this pharmaceutical composition are similar to those described above for the pharmaceutical composition for enhancing the moisture-retaining capacity of the skin.

According to this disclosure, the dosage and frequency of administration of the pharmaceutical composition for reducing oxidative stress may vary depending on the following factors: the severity of the oxidative stress to be treated, the route of administration, and the desired antioxidation effect to be achieved. For instance, the dosage of the pharmaceutical composition for topical administration according to this disclosure may be 1-10 mg/cm$^2$ of the skin area, and may be administered one to three times per day. In certain embodiments, the dosage of this pharmaceutical composition for oral administration may be 0.05-5 mg/Kg, and may be administered one to three times per day.

Due to the antioxidation activity regarding the hydrolysate of water extract of *Gracilariopsis chiangii* according to this disclosure, one can also predict that the hydrolysate of water extract of *Gracilariopsis chiangii* according to this disclosure may be effective in preventing and/or retarding skin aging. Accordingly, the composition provided in this disclosure can be used for preventing and/or retarding skin aging.

As used herein, the term "retarding" refers to treating, reducing, alleviating, ameliorating, relieving, or controlling one or more clinical signs of a disease or disorder, and lowering, stopping, or reversing the progression of severity regarding the condition or symptom being treated.

As used herein, the term "skin aging" is intended to encompass naturally occurring intrinsic skin aging and extrinsic skin aging caused by environmental factors (such as UV radiation). The symptoms of skin aging include, but are not limited to, telangiectasia, thinner epidermis, skin atrophy, poor skin texture, dryness, wrinkle formation and pigmentary change (such as lentigines, freckles, hypopigmentation or hyperpigmentation), etc.

Accordingly, the present disclosure further provides a method for preventing and/or retarding skin aging, which includes administering to a subject the composition described above. The composition may be administered to the subject in an effective amount for a sufficient time until at least one symptom of skin aging is significantly improved. The effective amount of the composition would not cause adverse side effects to the subject.

In certain embodiments, the composition for preventing and/or retarding skin aging is a pharmaceutical composition. The administration route, dosage and pharmaceutically acceptable carrier of this pharmaceutical composition are similar to those described above for the pharmaceutical composition for enhancing the moisture-retaining capacity of the skin.

The dosage and frequency of administration of the pharmaceutical composition for preventing and/or retarding skin aging may vary depending on the following factors: the severity of the symptom of skin aging to be treated, the route of administration, and the desired effect to be achieved. For instance, the dosage of the pharmaceutical composition for topical administration according to this disclosure may be 1-10 mg/cm$^2$ of the skin area, and may be administered one to three times per day. In certain embodiments, the dosage of this pharmaceutical composition for oral administration may be 0.05-5 mg/Kg, and may be administered one to three times per day.

Due to the above-mentioned biological activities and safety regarding the hydrolysate of water extract of *Gracilariopsis chiangii*, one can presume that the hydrolysate of water extract of *Gracilariopsis chiangii* can also be used as a cosmetic ingredient for a cosmetic composition. Therefore, in certain embodiments, the composition described above may be a cosmetic composition.

According to this invention, the cosmetic composition may further include a cosmetically acceptable adjuvant that is widely employed in cosmetic-manufacturing technology. For instance, the cosmetically acceptable adjuvant may include one or more of the following agents: solvents, gelling agents, activating agents, preservatives, antioxidants, screening agents, chelating agents, surfactants, coloring agents, thickening agents, fillers, fragrance and odor absorbents. The choice and amount of these additives are within the expertise of those skilled in the art.

The cosmetic composition provided in this disclosure can be prepared using technology well known to a skilled artisan into the form of skincare or makeup products. Such form includes, but is not limited to, aqueous solutions, aqueous-alcohol solutions or oily solutions, emulsions, gel, ointments, cream, masks, patches, packs, liniment, powder, aerosol, spray, lotions, serum, paste, foam, suspensions, drops, mousse, sunblock, tonic water, foundation, eyeshadow, makeup remover products, soaps and other body cleansing products.

The cosmetic composition of this disclosure can be used with at least one of the following external use agents: whitening agents (such as tretinoin, catechin, kojic acid, arbutin and vitamin C), humectants, anti-inflammatory agents, bactericides, ultraviolet absorbers, algal extracts (such as aloe extracts), skin nutrients, anesthetics, anti-acne agents, antipruritic, analgesic, antidermatitis agents, antihyperkeratolytic agents, anti-dry skin agents, antipsoriatic agents, antiaging agents, antiwrinkle agents, antiseborrheic agents, wound-healing agents, corticosteroid and hormone. The choice and amount of these agents are within the expertise of those skilled in the art.

The disclosure will be further described by way of the following examples. However, it should be understood that the following examples are solely intended for the purpose of illustration and should not be construed as limiting the disclosure in practice.

EXAMPLES

Example 1. Preparation of Hydrolysate of Water Extract of *Gracilariopsis chiangii*

3 to 9 grams of a *Gracilariopsis chiangii* alga harvested from Dapeng Bay (Pingtung County, Taiwan) was pulverized. The thus formed pulverized product of *Gracilariopsis chiangii* and water were mixed together in a weight ratio of 1:1.25 under heating at 50° C. for 1 hour, so as to obtain a water extract of *Gracilariopsis chiangii* (designated as WEGC hereinafter). Thereafter, bromelain (NEO-ONE BIOTECH Co., LTD, 1600 U/g, Cat. No. 1600GD) and the WEGC were reacted with each other in a weight ratio of 1:180 at 45° C. for 4 hours. The reaction mixture was subjected to filtration sequentially using a filter bag having a pore size of 5 μm and two filter cartridges having pore sizes of 1 μm and 0.5 μm (TECH SEED ENTERPRISE CO., LTD.), followed by lyophilization. Thus, a hydrolysate of water extract of *Gracilariopsis chiangii* (designated as HWEGC hereinafter), which was in powder form, was formed.

For comparison with HWEGC, a *Gracilaria* tenuistipitata alga, harvested from Kouhu Township (Yunlin County, Taiwan), was used to prepare a hydrolysate of water extract of *Gracilaria tenuistipitata* (designated as HWEGT hereinafter) in powder form according to the same process as mentioned above.

Example 2. HPLC Analysis for Hydrolysate of Water Extract of *Gracilariopsis chiangii*

To understand the major components in the hydrolysate of water extract of *Gracilariopsis chiangii*, the HWEGC prepared according to the above Example 1 was dissolved in distilled deionized water to obtain a test sample having a HWEGC concentration of 1 mg/mL, and then a HPLC (high performance liquid chromatography) analysis was conducted.

The HPLC instruments employed are as follows: Agilent/HP 1100 HPLC System equipped with a UV-Vis detector and a C18 column (Purospher® STAR RP-18, Cat. No. 150359, size: 250 mm×4.6 mm).

The operating conditions of HPLC applied are described as follows. Mobile phase is acetonitrile/deionized water (100:0, v/v), and the flow rate of the mobile phase is 0.7 mL/min. Gradient elution with the mobile phase was conducted for 35 minutes as follows: acetonitrile was decreased from 100% to 90% during 0-10 minutes, was decreased from 90% to 80% during 10-30 minutes, was increased from 80% to 100% at 30 minute, and was maintained at 100% during 30-35 minutes.

Results:

FIG. 1 is a HPLC elution profile of the HWEGC prepared in Example 1. As shown in FIG. 1, three major peaks (respectively labeled with a, b and c) can be found between a retention time of 0 minute and a retention time of 35 minutes.

Example 3. Evaluation for Antioxidation Efficacy of HWEGC

In order to investigate the antioxidation efficacy of the HWEGC according to this disclosure, the HWEGC obtained in the above Example 1 was subjected to α,α-diphenyl-β-picrylhydrazyl (DPPH) free radical-scavenging assay and reducing ability determination with Prussian blue.

Experimental Procedures:
A. DPPH Free Radical-Scavenging Assay

Five HWEGC samples respectively having HWEGC concentrations of 100, 300, 500, 700 and 900 μg/mL were prepared. Specifically, for preparing each of the five HWEGC samples, a suitable amount of the HWEGC prepared in Example 1 was dissolved in distilled deionized water.

For comparison with the five HWEGC samples, five HWEGT samples (respectively having HWEGT concentrations of 100, 300, 500, 700 and 900 μg/mL) and four WEGC samples (respectively having WEGC concentrations of 100, 300, 500 and 700 μg/mL) were also prepared. Specifically, for preparing each of the five HWEGT samples and four WEGC samples, a suitable amount of the HWEGT or WEGC prepared in Example 1 was dissolved in distilled deionized water.

Thereafter, 1 mL of a respective sample and 1 mL of a 90% ethanol solution (served as a control sample) were each mixed with 0.1 mM DPPH in ethanol (1 mL), followed by incubation at 25° C. in the absence of light for 1 hour. Then, the absorbance at 517 nm ($OD_{517}$) was measured for each resulting mixture using a spectrophotometer. A lower $OD_{517}$ value indicates that the sample tested has a stronger free radical-scavenging ability.

The DPPH free radical-scavenging ability (%) was calculated using the following Equation (I):

$$A=[1-(B/C)]\times 100 \quad (I)$$

where A=the DPPH free radical-scavenging ability (%)
  B=$OD_{517}$ of a respective one of the HWEGC samples, the HWEGT samples and the WEGC samples
  C=$OD_{517}$ of the control sample The experimental data are expressed as mean±SD (standard deviation). The experimental data were analyzed using Student's test so as to assess the difference between the samples tested. Statistical significance is indicated by p<0.05.

B. Reducing Ability Determination

The four HWEGC samples (respectively having HWEGC concentrations of 100, 300, 500 and 700 μg/mL), the four HWEGT samples (respectively having HWEGT concentrations of 100, 300, 500 and 700 μg/mL) and the four WEGC samples (respectively having WEGC concentrations of 100, 300, 500 and 700 μg/mL) prepared in the above section A of this example were used in this experiment.

To be specific, 0.1 mL of a respective sample was added to 0.4 mL of a 100% ethanol solution, followed by mixing with 0.5 mL of a phosphate buffer solution (0.2 M; pH 6.6) and 0.5 mL of a 1% potassium ferricyanide solution. After the reaction proceeded at 50° C. for 20 minutes, 0.5 mL of a 10% trichloroacetic acid solution was added, followed by centrifugation at 3000 rpm for 10 minutes. The obtained supernatant was mixed with 1 mL of distilled water and 0.2 mL of a 0.1% ferric chloride solution, followed by incubation at 25° C. in the absence of light for 10 minutes. Thereafter, the absorbance at 700 nm ($OD_{700}$) was measured for each resulting mixture using a spectrophotometer. A higher $OD_{700}$ value indicates that the sample tested has a stronger reducing ability. Furthermore, a 1 mg/mL dibutyl hydroxyl-toluene (BHT) solution serving as a control sample was also subjected to the aforementioned procedures for $OD_{700}$ measurement.

The reducing ability (%) was calculated using the following Equation (II):

$$D=(E/F)\times 100 \quad (II)$$

where D=the reducing ability (%)
  E=$OD_{700}$ of a respective one of the HWEGC samples, the HWEGT samples and the WEGC samples
  F=$OD_{700}$ of the control sample The experimental data are expressed as mean±SD. The experimental data were analyzed using Student's test so as to assess the difference between the samples tested. Statistical significance is indicated by p<0.05.

Figure 2:
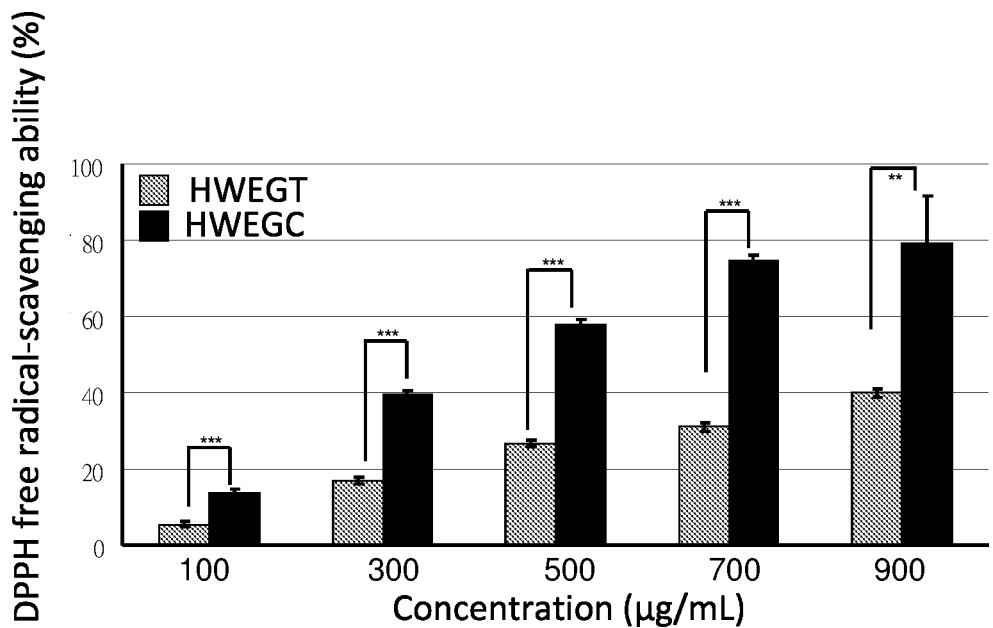
FIG. 2 shows the DPPH free radical-scavenging ability (%) regarding the HWEGC and a hydrolysate of water extract of *Gracilaria tenuistipitata* (designated as HWEGT) prepared in Example 1 at different concentrations, in which the symbols "" and "*" respectively represent $p<0.01$ and $p<0.001$.
Figure 3:
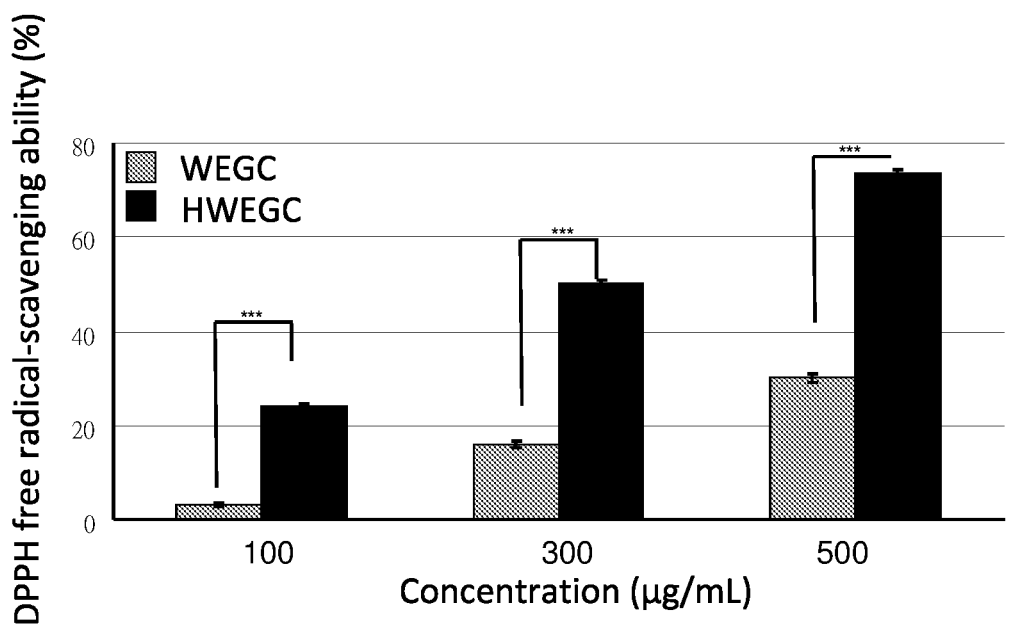
FIG. 3 shows the DPPH free radical-scavenging ability (%) regarding the HPGC and a water extract of *Gracilariopsis chiangii* (designated as WEGC) prepared in Example 1 at different concentrations, in which the symbol "***" represents $p<0.001$.

Results:

FIGS. 2 and 3 show the DPPH free radical-scavenging ability (%) of the different concentrations of HWEGC, HWEGT and WEGC. As shown in FIGS. 2 and 3, the DPPH free radical-scavenging ability of the HWEGC at each concentration is significantly higher than that of the HWEGT and WEGC at any concentration. In particular, as the concentration of HWEGC increases, the DPPH free radical-scavenging ability exhibited becomes higher.

Figure 4:
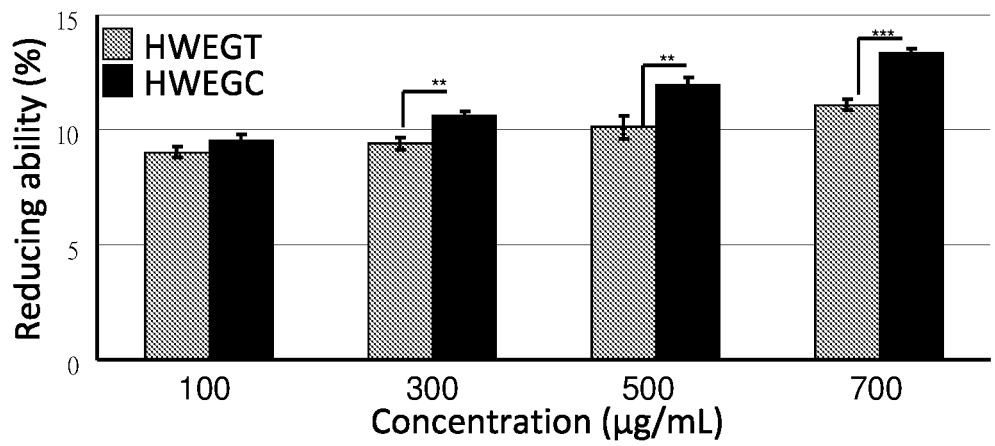
FIG. 4 shows the reducing ability (%) regarding the HWEGC and HWEGT prepared in Example 1 at different concentrations, in which the symbols "" and "*" respectively represent $p<0.01$ and $p<0.001$.
Figure 5:
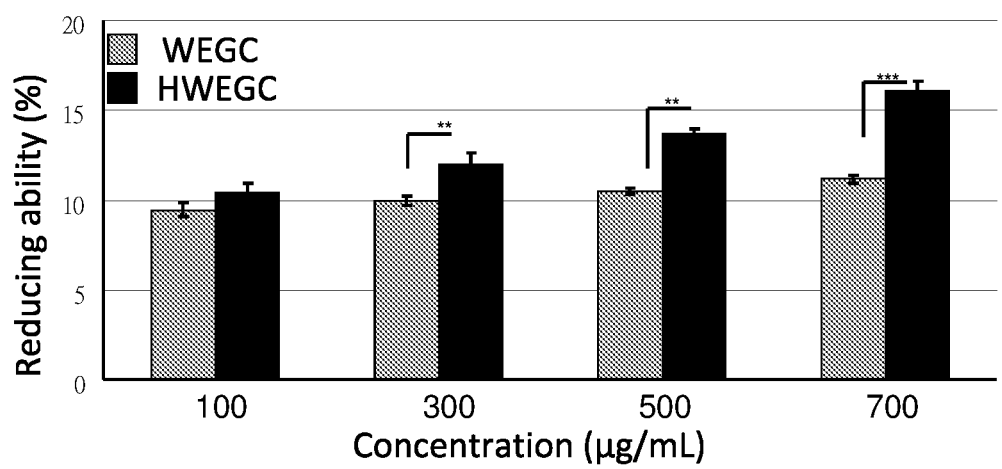
FIG. 5 shows the reducing ability (%) regarding the HWEGC and WEGC prepared in Example 1 at different concentrations, in which the symbols "" and "*" respectively represent $p<0.01$ and $p<0.001$.

FIGS. 4 and 5 show the reducing ability (%) of the different concentrations of HWEGC, HWEGT and WEGC. It can be seen from FIGS. 4 and 5 that, at most of concentrations, the reducing ability of the HWEGC is significantly higher than that of the HWEGT and WEGC. In particular, as the concentration of HWEGC increases, the reducing ability exhibited becomes higher.

The above experimental results reveal that the HWEGC of this disclosure, which was obtained by subjecting the WEGC to a hydrolysis treatment with bromelain, exhibits a more excellent antioxidation activity compared to the WEGC. In addition, the HWEGC of this disclosure is more effective in antioxidation as compared to the HWEGT, even though these two hydrolysates were prepared using the same process. Consequently, the applicants deduce that the HWEGC of this disclosure can serve as antioxidants and free radical scavengers for reducing oxidative stress.

Example 4. Evaluation for Effects of HWEGC on Improvement of Wound Healing

In order to investigate the effects of the HWEGC according to this disclosure on wound healing, the HWEGC obtained in the above Example 1 was subjected to wound-healing cell migration assay in this example. Furthermore, the HWEGT and WEGC obtained in the Example 1 were also subjected to the same assay for comparison purpose.

Experimental Materials:

A. Human Skin Fibroblast Cell Line Detroit 551

Human skin fibroblast cell line Detroit 551 used in this example was purchased from Biosource Collection and Research Center (BCRC) of Food Industry Research and Development Institute (FIRDI) (331 Shih-Pin Road, Hsinchu 300, Taiwan).

Detroit 551 cells were incubated in a Petri dish containing a minimum essential medium (MEM, Product No. M2279; Sigma; MO, USA) supplemented with 10% fetal bovine serum (FBS) and 1% penicillin-streptomycin (Gibco™, Cat. No. 15140122), followed by cultivation in an incubator with culture conditions set at 37° C. and 5% $CO_2$. Medium change was performed every two days. Cell passage was performed when the cultured cells reached 80%-90% of confluence.

Experimental Procedures:

First, the Detroit 551 cells were divided into 4 groups including a control group, an experimental group (i.e., HWEGC group) and two comparative groups (i.e. HWEGT group and WEGC group). Each group of Detroit 551 cells was incubated in a 24-well plate containing 500 μL MEM (supplemented with 10% FBS and 1% penicillin-streptomycin), followed by cultivation in an incubator (37° C., 5% $CO_2$). After medium change with a fresh medium, a plastic pipette tip of 200 μL was used to scratch the Detroit 551 cells in each well of the plate along a diametral line. Therefore, a wound zone having a width of 500 μm and no cells attached thereto was formed along a diametral line of each well. After washing twice with PBS and then conducting medium change with a fresh MEM (supplemented with 0.5% FBS and 1% penicillin-streptomycin), the cell cultures of HWEGC, HWEGT and WEGC groups were respectively treated with suitable amounts of the HWEGC, HWEGT and WEGC obtained in Example 1 so that the cell cultures of HWEGC, HWEGT and WEGC groups respectively had final concentrations of 0.03% (w/w) HWEGC, 0.03% (w/w) HWEGT and 0.03% (w/w) WEGC. Then, the treated Detroit 551 cells in each group were cultivated in an incubator (37° C., 5% $CO_2$) for 12 hours. At 0 hour and 12 hour after the treatment, the wound zones of each group were observed using an inverted microscope (NIKON TE300, Japan) under 40× magnification, were photographed using a digital camera (Nikon F90, Japan), and were subjected to area calculation using ImageJ software.

The wound healing percentage (%) was calculated using the following Equation (III):

$$G=[1-(H/I)]\times 100 \quad (III)$$

where G=the wound healing percentage (%)
H=the area of the wound zone at 12 hour after the treatment
I=the area of the wound zone at 0 hour after the treatment
All experiments were repeated twice. The experimental data are expressed as mean±SD, and were analyzed using Student's test so as to assess the difference between the test groups. Statistical significance is indicated by $p<0.05$.

Figure 6:
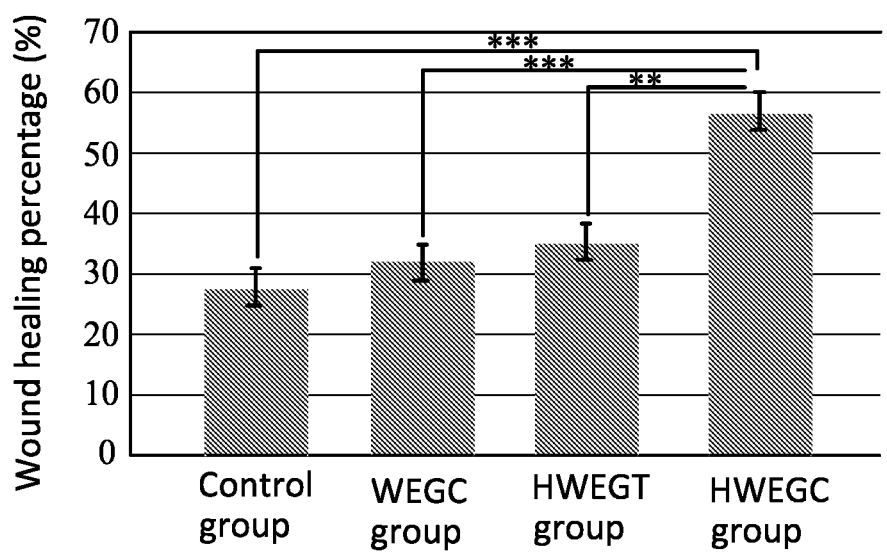
FIG. 6 shows the effects of the WEGC, HWEGT and HWEGC prepared in Example 1 on the wound healing of fibroblasts, in which the symbols "" and "*" respectively represent $p<0.01$ and $p<0.001$.

Results:
FIG. 6 shows the wound healing percentage of the Detroit 551 cells treated with HWEGC, HWEGT and WEGC.

As shown in FIG. 6, there is no apparent difference in the wound healing percentage of Detroit 551 cells between the control group, WEGC group and HWEGT group. However, the wound healing percentage of Detroit 551 cells in HWEGC group is significantly higher as compared with that in the control group and that in the two comparative groups. The experimental results reveal that the HWEGC of this disclosure is effective in promoting fibroblast-mediated wound closure, thereby being able to improve wound healing.

Example 5. Evaluation for Effects of HWEGC on Enhancement of the Moisture-Retaining Capacity of Skin In order to investigate the effects of the HWEGC according to this disclosure on enhancement of the moisture-retaining capacity of the human skin, the following experiments were performed.

A. Preparation of Essences

The HWEGC and WEGC obtained in Example 1 were used in this example. Three essences (including a HWEGC essence, a WEGC essence and a control essence) were respectively formulated using the ingredients in a given amount as shown in Table 1.

TABLE 1

| Ingredients | HWEGC essence | WEGC essence | Control essence |
| --- | --- | --- | --- |
| Butylene glycol# | 1 | 1 | 1 |
| Hydroxyethyl cellulose# | 0.3 | 0.3 | 0.3 |
| Dermosoft OMP* | 3 | 3 | 3 |
| HWEGC | 4 | — | — |
| WEGC | — | 4 | — |
| Deionized water | 91.7 | 91.7 | 95.7 |

The amount of each ingredient is expressed as % (w/w).
purchased from First Chemical Co., Ltd.
*purchased from HonorChem Co., Ltd.

The procedure for the preparation of the HWEGC essence and WEGC essence is described in more detail as follows. First, butylene glycol and hydroxyethyl cellulose were dissolved in deionized water at 75° C. under agitation. After cooling to 40° C.-45° C., HWEGC or WEGC was added, followed by mixing with Dermasoft OMP under agitation. Then, the pH value of the resulting mixture was adjusted to between 6 to 7 with NaOH, so as to obtain the HWEGC essence and WEGC essence.

The procedure for the preparation of the control essence is similar to that for the HWEGC essence, except deionized water is used instead of HWEGC.

B. Screening of Test Subjects

Subjects enrolled from Yeun Diing Enterprise CO., LTD. (Pingtung county, Taiwan) and M.H. Biotechnology Co., Ltd. (Yunlin County, Taiwan) were subjected to selection according to the exclusion criteria outlined in Table 2. A total of 10 eligible test subjects, including 4 males and 6 females at an age ranging from 25 to 40 years, participate in the following test.

TABLE 2

| No. | Exclusion criteria |
| --- | --- |
| 1 | Possession of sensitive skin. |
| 2 | Possession of a skin disease, such as eczema, atopic dermatitis and allergic dermatitis |
| 3 | Pregnancy. |
| 4 | Use of other skin care products containing a moisture-retaining component during the test |

C. Pre-Clinical Test

The right arm of each of the test subjects was randomly divided into three test areas having a width of 4 fingerbreadths, i.e., a HWEGC test area, a WEGC test area and a control test area onto which the HWEGC essence, the WEGC essence and the control essence prepared in section A of this example were respectively applied at a dose of 0.5 mL twice daily. The test period for each test area lasted a total of 28 days.

D. Determination of Water Content of Stratum Corneum

The test areas of each test subject at Day 0 (i.e., prior to the application of the test essences) and at a designated time point (Days 7, 14, 21 and 28) after the beginning of the application of the test essences were separately subjected to determination of the water content of stratum corneum using a capacitance meter (Corneometer® CM 285, Courage & Khazaka).

The percent improvement of the water content of stratum corneum was calculated using the following Equation (IV):

$$J=[(L-K)/K]\times 100 \quad (IV)$$

where J=the percent improvement of the water content of stratum corneum at the designated time point (Days 7, 14, 21 and 28)
K=the water content of stratum corneum at Day 0
L=the water content of stratum corneum at the designated time point The test areas of each test subject were repeatedly subjected to the water content determination 3 times. The experimental data are expressed as mean±SD and were analyzed using Student's test so as to assess the difference between the test areas. Statistical significance is indicated by $p<0.05$.

E. Safety Evaluation Safety evaluation was conducted by a researcher at Day 0 and at a designated time point thereafter (Days 7, 14, 21 and 28). On Day 0, small amounts of the essences were applied onto an inner side of an upper arm portion for safety evaluation only. The test subjects were surveyed by the researcher in respect to the occurrence of any adverse skin response (including itchiness, irritation and erythema).

Results:

A. Determination of Water Content of Stratum Corneum

Figure 7:
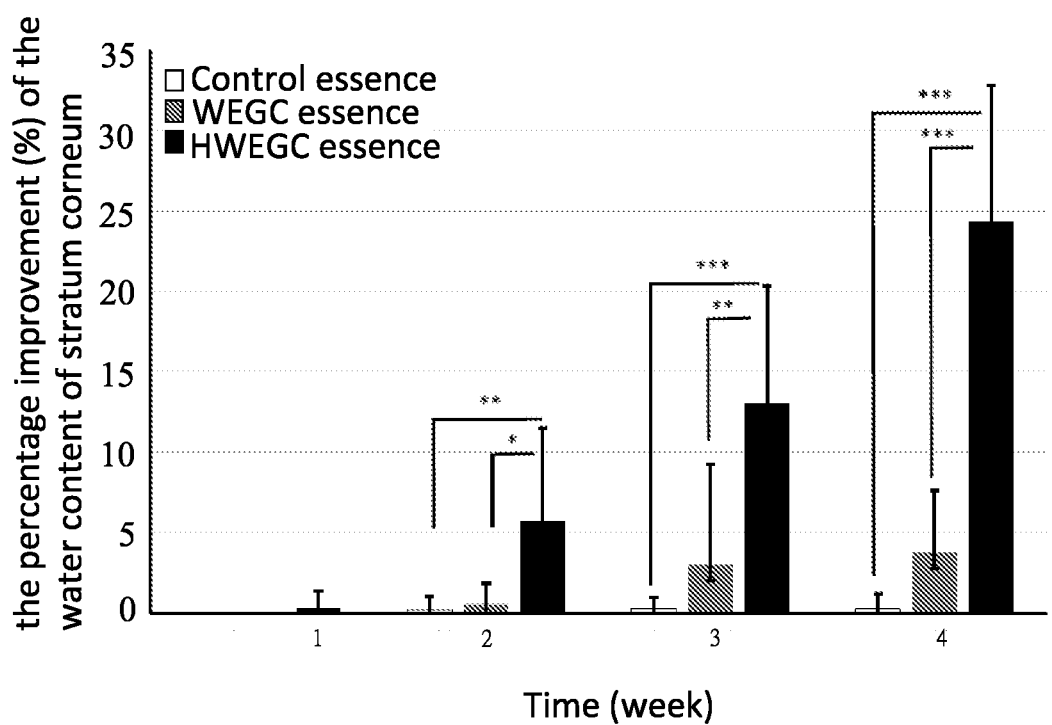
FIG. 7 shows the effects of a HWEGC essence (formulated with the HWEGC prepared in Example 1), a WEGC essence (formulated with the WEGC prepared in Example 1) and a control essence (containing no HWEGC or WEGC) upon improvement in the water content of stratum corneum, in which the symbols "*", "" and "*" respectively represent $p<0.05$, $p<0.01$ and $p<0.001$.

FIG. 7 shows the percent improvement of the water content of stratum corneum in each test area with time. As shown in FIG. 7, at Days 14, 21 and 28 after the beginning of the application of the test essences, the percent improvement of the water content of stratum corneum in the HWEGC test area is significant higher than that in the WEGC test area and the control test area. In addition, the water content of stratum corneum in the HWEGC test area dramatically increased with time, while the improvement in the WEGC test area is quite slow. These data suggest that the HWEGC of this disclosure can be used to effectively enhance the moisture-retaining capacity of the skin.

B. Safety Evaluation of HWEGC Essences

During the test period, no adverse skin response was observed on all the test subjects with the HWEGC essence (data not shown) applied thereto.

In view of the foregoing, the HWEGC according to this disclosure can exhibit an excellent anti-oxidation activity, promote wound healing and enhance the moisture-retaining capacity of the skin. Therefore, the applicants deem that the HWEGC according to this disclosure can be developed into a skin care product for long-term use which does not induce adverse side effects.

All patents and references cited in this specification are incorporated herein in their entirety as reference. Where there is conflict, the descriptions in this case, including the definitions, shall prevail.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A process for preparing a hydrolysate of a water extract of *Gracilariopsis chiangii*, comprising the steps of:
    subjecting an alga of *Gracilariopsis chiangii* to an extraction treatment with water to obtain a water extract; and
    subjecting the water extract to a hydrolysis treatment with bromelain.

2. The process of claim 1, wherein the weight ratio of the alga of *Gracilariopsis chiangii* to water in a range from 1:0.5 to 1:5.

3. The process of claim 1, wherein the weight ratio of bromelain to the water extract in a range from 1:50 to 1:500.

4. The process of claim 1, further comprising the steps of a solid-liquid separation treatment after the hydrolysis treatment to remove a solid portion resulting from the hydrolysis treatment.

5. A hydrolysate of a water extract of *Gracilariopsis chiangii*, wherein the hydrolysate is obtained by the process comprising the steps of:
    subjecting an alga of *Gracilariopsis chiangii* to an extraction treatment with water to obtain a water extract; and
    subjecting the water extract to a hydrolysis treatment with bromelain.

6. The hydrolysate of claim 5, wherein the weight ratio of the alga of *Gracilariopsis chiangii* to water in a range from 1:0.5 to 1:5.

7. The hydrolysate of claim 5, wherein the weight ratio of bromelain to the water extract in a range from 1:50 to 1:500.

8. The hydrolysate of claim 5, wherein the process further comprises the step of a solid-liquid separation treatment after the hydrolysis treatment to remove a solid portion resulting from the hydrolysis treatment.

9. A composition comprising the hydrolysate according to claim 5.

10. The composition of claim 9, wherein the composition enhances the moisture-retaining capacity of the skin.

11. The composition of claim 9, wherein the composition enhances the moisture-retaining capacity of the skin.

12. The composition of claim 9, wherein the composition improves wound healing.

13. The composition of claim 9, wherein the composition reduces oxidative stress.

14. The composition of claim 9, wherein the composition is in a topical dosage form.

15. The composition of claim 9, wherein the composition is in an oral dosage form.

* * * * *